United States Patent
Ruan et al.

(10) Patent No.: US 8,837,674 B2
(45) Date of Patent: Sep. 16, 2014

(54) METHOD FOR REDUCING DIAGNOSTIC RADIATION DOSE IN IMAGE GUIDED RADIOTHERAPY

(75) Inventors: Dan Ruan, Los Angeles, CA (US); Paul J. Keall, Greenwich (AU)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 321 days.

(21) Appl. No.: 13/199,366

(22) Filed: Aug. 26, 2011

(65) Prior Publication Data
US 2012/0076270 A1    Mar. 29, 2012

Related U.S. Application Data

(60) Provisional application No. 61/402,346, filed on Aug. 27, 2010.

(51) Int. Cl.
*A61N 5/10* (2006.01)

(52) U.S. Cl.
CPC ....... *A61N 5/1049* (2013.01); *A61N 2005/1061* (2013.01)
USPC ............................................. 378/65

(58) Field of Classification Search
USPC ................................................. 378/65
See application file for complete search history.

*Primary Examiner* — Jurie Yun
(74) *Attorney, Agent, or Firm* — Lumen Patent Firm

(57) ABSTRACT

A method of minimizing radiation toxicity in image guided radiotherapy (IGRT) is provided that includes using a probabilistic prediction algorithm that is operated on a suitably programmed computer and includes multimodality inputs and provides real-time geometric and topological target estimates to compensate for system latency, using an online adaptive imaging system that provides radiographic images of the target when the geometric and topological target estimates are in a region of predefined uncertainty, and using an image dose control algorithm, operating on a suitably programmed computer, that includes parameters for controlling dose per image, where instances for image acquisition are optimized according to a planned dose pattern and delivery result.

8 Claims, 2 Drawing Sheets

METHOD FOR REDUCING DIAGNOSTIC RADIATION DOSE IN IMAGE GUIDED RADIOTHERAPY

CROSS-REFERENCE TO RELATED APPLICATIONS

This application claims priority from U.S. Provisional Patent Application 61/402,346 filed Aug. 27, 2010, which is incorporated herein by reference.

FIELD OF THE INVENTION

The present invention relates generally to radiotherapy. More particularly, the invention relates to a method of accounting for the accumulative effect of imaging dose and treatment dose in image guided radiotherapy (IGRT) using adaptive imaging to minimize radiation toxicity without compromising delivery accuracy.

BACKGROUND OF THE INVENTION

The philosophy that diagnostic dose should be accounted for in radiotherapy planning and treatment is widely recognized, where reduction of imaging dose with ensured adaptive delivery accuracy, deceases the risk of tissue toxicity. However, optimization of a system that embodies such principle has been problematic due to target motion and beam guidance.

What is needed is motion-adaptive image guided radiotherapy for improving the agreement between planned dose pattern and delivery result, to ensure tumor target coverage and reduce likelihood of tissue toxicity.

SUMMARY OF THE INVENTION

To address the needs in the art, a method of minimizing radiation toxicity in image guided radiotherapy (IGRT) is provided that includes using a probabilistic prediction algorithm, operating on a suitably programmed computer, that includes multimodality inputs and provides real-time geometric and topological target estimates to compensate for system latency, using an online adaptive imaging system that provides radiographic images of the target when the geometric and topological target estimates are in a region of pre-defined uncertainty, and using an image dose control algorithm, operating on a suitably programmed computer, that includes parameters for controlling dose per image, where instances for image acquisition are optimized according to a planned dose pattern and delivery result.

According to one aspect of the invention, the probabilistic prediction algorithm provides an uncertainty quantity associated with the real-time geometric and topological target estimates.

In another aspect of the invention, the probabilistic prediction algorithm includes a Kernel Density Estimation (KDE)-based prediction algorithm and the associated uncertainty estimate based on probability inference.

In a further aspect of the invention, a resource allocation algorithm provides retrospective optimization and generates performance bounds.

According to another aspect of the invention, a real-time dose control algorithm is operated on the suitably programmed computer to provide prospective optimization for an imaging sequence and an imaging technique based on geometry and topology estimates and geometry and topology estimate uncertainties and a planned dose pattern and accumulative delivery results at an instant of time, where the imaging sequence includes triggers, and where the imaging technique includes voltage, tube current and pulse settings.

In a further aspect of the invention, a real-time dose control algorithm provides prospective optimization for the imaging sequence (triggers) and imaging technique (voltage, tube current and pulse settings) based on the geometry and topology estimate and their uncertainties, and the planned dose pattern and accumulative delivery results at the instant of time.

In yet another aspect of the invention, the multimodality inputs can include optical reading, kV/MV imaging, a moveable gantry, radiotherapy beam or multi-leaf collimator.

According to another aspect of the invention, the method is operated offline and online, where the online operation provides in motion-adaptive image guided radiotherapy used for improving the agreement between planned dose pattern and delivery result, and reduced likelihood of tissue toxicity.

In another aspect of the invention, uncertainty quantities of the geometric and topological estimates are obtained in real-time by a suitable prediction algorithm.

DETAILED DESCRIPTION

Figure 1:
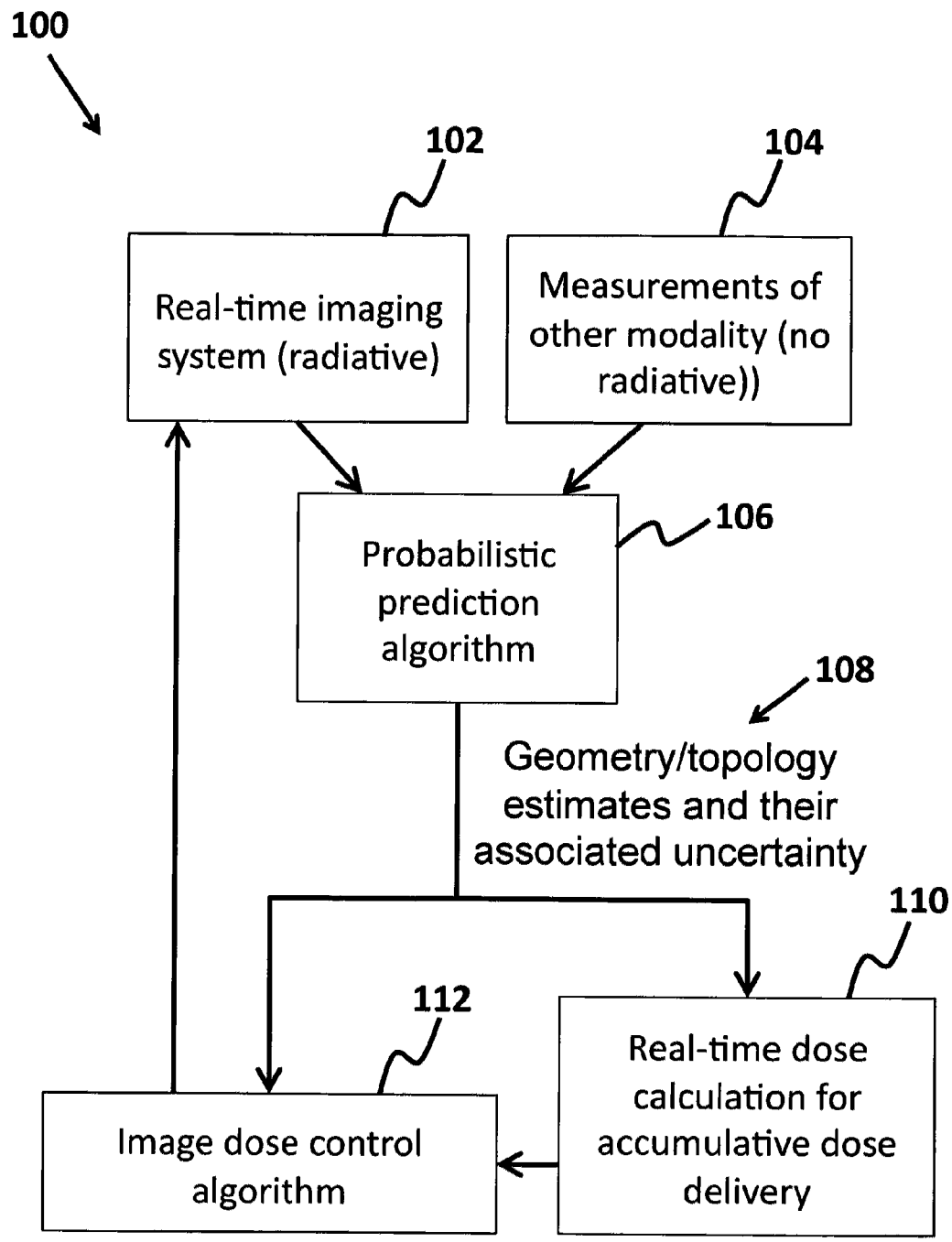
FIG. 1 shows a flow diagram of the method minimizing radiation toxicity in image guided radiotherapy (IGRT), according to one embodiment of the invention.

According to one embodiment of the invention, a method of minimizing radiation toxicity in image guided radiotherapy (IGRT) is provided that includes using a hybrid online data acquisition system to monitor the geometry and topology of a treatment region, from both non-radiation modalities (optical, pressure, implanted electromagnetic sensors etc.) and radiographic modality; using a probabilistic prediction algorithm, operating on a suitably programmed computer, that processes real-time multimodality input from the hybrid online data acquisition system and provides real-time geometric and topological target estimates to compensate for system latency required for adapting the control in radiotherapy; an imaging dose control algorithm, operating on a suitably programmed computer, that provides real-time parameters for controlling imaging time (triggers), imaging technique (voltage, tube current, pulse width etc), which optimizes image acquisition according to the online estimated geometry/topology, their associated uncertainty and the planned dose pattern and accumulative delivery results at the instant of processing.

According to one aspect of the invention, the probabilistic prediction algorithm provides real-time geometric and topologic estimates of the target, and quantifies the estimates' uncertainty at the same time.

According to one embodiment, the invention provides instantaneous online decisions on imaging excitation, flux level, imager configuration parameters and provides the corresponding expected dose deviation from such scheme.

In another embodiment, the invention provides a global optimality metric in dose delivery that is formulated systematically to account for the accumulative effect of diagnostic radiation and treatment radiation. Utilizing the observation that the region affected by imaging radiation is almost complementary to the treatment plan and delivery, the imaging dose is treated as a "cost" that should be controlled to avoid tissue toxicity during image guided radiotherapy. Combined with a probabilistic prediction algorithm having hybrid (multimodality) inputs that compensate for system latency, an online adaptive imaging system is devised so that radiographic images are only taken when the instantaneous geometric and topological estimate suffers from high uncertainty. The optimization setup is formulated in terms of dose difference, and reflects clinical endpoint. Parameters for controlling dose per image and instances for imaging acquisition are optimized with respect to the defined objective. Retrospective optimization is found to be closely associated with a typical resource allocation, where a solution analogous to the classic "reverse water filling" scheme is provided. The online optimization scheme is formulated and efficiently solved in a dynamic programming framework.

In another embodiment, the invention can be used with an image guided radiotherapy system, particularly for aggressive motion-compensating systems with high efficiency.

In a further embodiment, the invention explicitly accounts for the combined effect of diagnostic dose and treatment dose. Adaptive imaging based on estimation accuracy provides quality assurance uniformly on the delivery efficacy throughout the whole duration of treatment. It realizes the core principles in radiation imaging "as low as reasonably achievable" with ensured delivery accuracy.

In another embodiment, the invention allows for the extension to hybrid (multimodality) inputs, including optical reading, kV/MV imaging. It is also compatible with various prediction options, as long as the predictor provides simultaneously an estimate of the state and the associated error/uncertainty.

Even though the philosophy that diagnostic dose should be accounted for in planning and treatment is widely recognized, the invention embodies such principle in system design and online optimization. The clinical endpoint aligned optimization, the interpretation in terms of resource allocation (both offline and online), and the corresponding solutions are all novel components.

According to another embodiment, the computer operated algorithms include Kernel density estimation (kde) based prediction algorithm and the associated uncertainty estimate based on probability inference, resource allocation algorithm for retrospective optimization and the generation of performance bounds, and a dynamic programming algorithm for online planning.

The method according to one embodiment of the invention provides instantaneous online decisions on imaging excitation, flux level, imager configuration parameters and provides the corresponding expected dose deviation from such scheme. The invention provides in motion-adaptive image guided radiotherapy for improving the agreement between planned dose pattern and delivery result, and reduced likelihood of tissue toxicity.

In a further aspect of the invention, the geometric/topological estimates and their uncertainty are obtained in real-time by other suitable prediction approaches. The online adaptive imaging system is then used to provide radiographic images of the target when the geometric and topological target estimates are in the region of the predefined uncertainty. Then, the image dose control algorithm includes the parameters for controlling dose per image, where instances for image acquisition are optimized according to a planned dose pattern and delivery result.

The advantages of the invention include: a system to account for diagnostic dose in an integrated fashion, an efficient online optimization, a system that is compatible to various data input modalities, and a system that is compatible when various selections of prediction algorithms are applied.

Turning to the figures, FIG. 1 shows a flow diagram of the method 100 minimizing radiation toxicity in image guided radiotherapy (IGRT), according to one embodiment of the invention. The method includes using a real-time imaging system (radiative) 102 and measurements of other non-radiative modalities 104 that are integrated to operate according to a probalilistic prediction algorithm 106 probabilistic prediction algorithm, operating on a suitably programmed computer, wherein geometry (topology) estimates and their associated uncertainties 108 are output for real-time dose calculation for accumulative dose delivery 110, and output for use in an image dose control algorithm 112, where the real-time dose calculation for accumulative dose delivery 110 is output to the image dose control algorithm 112, where the results from the image dose control algorithm 112 are output to the real-time imaging system (radiative) 102.

Figure 2:
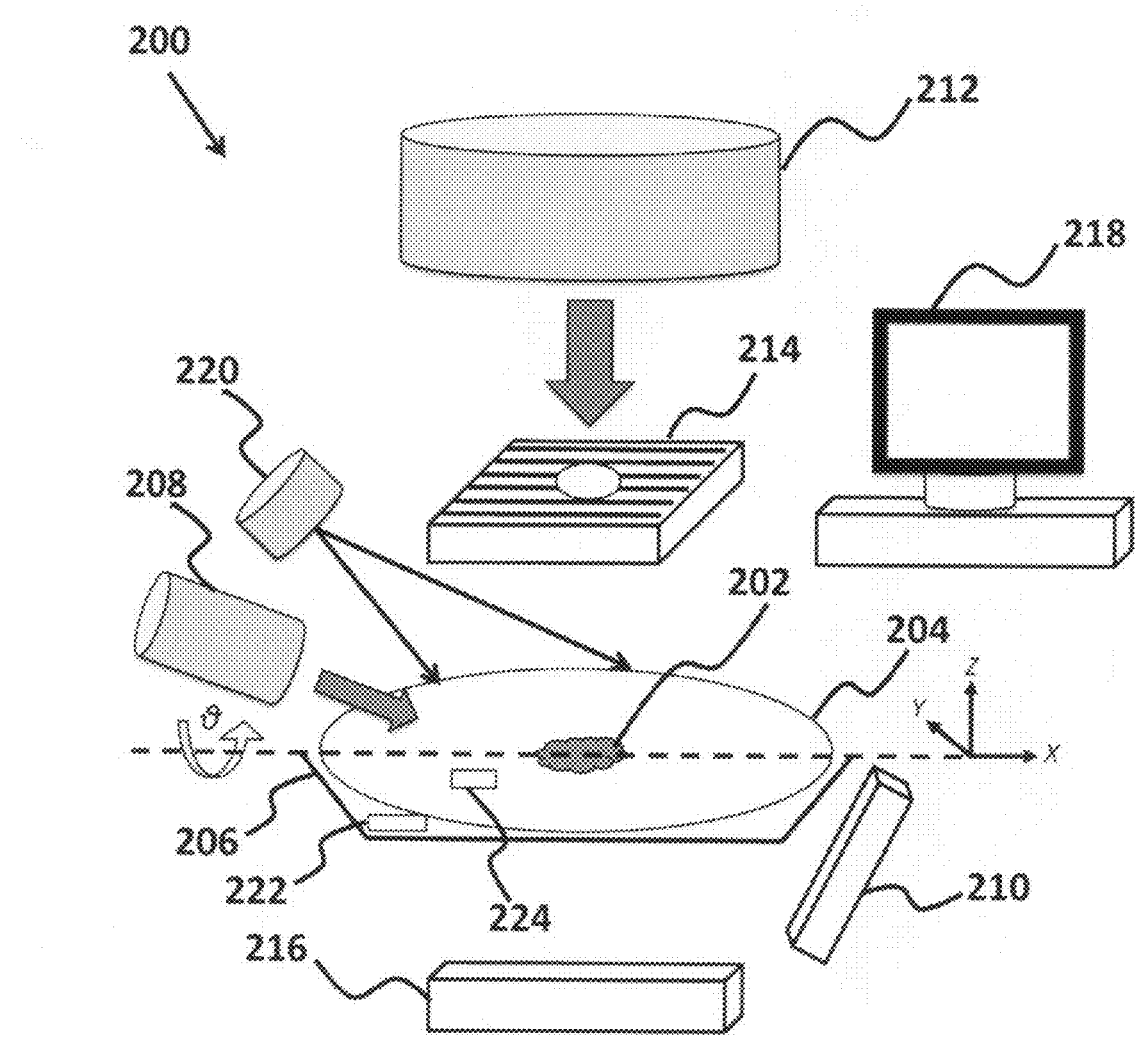
FIG. 2 shows a schematic drawing of a treatment apparatus used to implement the method of minimizing radiation toxicity in image guided radiotherapy (IGRT), according to one embodiment of the invention.

FIG. 2 shows a schematic drawing of a treatment apparatus 200 that could be implemented to use the method 100 minimizing radiation toxicity in image guided radiotherapy (IGRT), according to one embodiment of the invention. As shown, a target 202 is disposed in a subject 204 disposed on a gantry 206, where the gantry 206 has translational (x, y), vertical (z) and rotational (θ) degrees of freedom. A kV imaging source 208 and a kV detector 210 are disposed to monitor the target 202 under optimization by the invention. A dosed delivery source 212 operates to irradiate the target 202 when directed through a multi-leaf collimator 214. As further shown, an appropriately programmed computer 218 operating a probabilistic prediction algorithm, and an image dose control algorithm operates the multiple modalities that include optical detectors 220, kV imaging 208/210, the moveable gantry 206, radiotherapy beam 212, multi-leaf collimator 214, pressure sensors 222, and implanted electromagnetic sensors 224, where the radiation dose is obtained by monitoring the target geometry/topology from hybrid observations above and performing real-time dose distribution calculation using the delivery parameters (from machine/plan) and the instantaneous geometry.

Here, the instances for image acquisition are optimized according to a planned dose pattern and delivery result.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, variations can include the incorporation of other real-time monitoring modalities as they become available, such as radiative-implantation-based tracking system, real-time MRI imaging. As another example, rather than controlling the imaging parameters continuously in real-time, the invention can be applied with minor modification to switch among pre-programmed imaging control sequences.

All such variations are considered to be within the scope and spirit of the present invention as defined by the following claims and their legal equivalents.

What is claimed:

1. A method of minimizing radiation toxicity in image guided radiotherapy (IGRT), comprising:
   a. using a hybrid online data acquisition system to monitor a geometry and a topology of a treatment region from a non-radiation modality, a radiation modality, or said non-radiation modality and said radiation modality;
   b. using a probabilistic prediction algorithm operating on a suitably programmed computer to process a real-time multimodality input from said online data acquisition system, wherein said probabilistic prediction algorithm provides real-time geometric and topological target estimates to compensate for a latency of said online data acquisition system;

c. using an online adaptive imaging system, wherein online adaptive imaging of said online adaptive imaging system is used to obtain radiographic images of a target when said real-time geometric and topological target estimates are in a region of predefined uncertainty; and d. using an image dose control algorithm operating on said suitably programmed computer to obtain real-time parameters to control a dose per image, wherein instances for image acquisition are optimized according to a planned dose pattern and delivery result according to said real-time geometric and topological target estimates, said predefined uncertainty, said planned dose pattern and accumulative delivery results at a processing instance.

2. The method according to claim 1, wherein said probabilistic prediction algorithm simultaneously quantifies said uncertainties in said estimates.

3. The method according to claim 1, wherein said probabilistic prediction algorithm comprises a Kernel Density Estimation (KDE)-based prediction algorithm and an associated uncertainty estimate based on probability inference.

4. The method according to claim 1, wherein a resource allocation algorithm provides retrospective optimization and generates performance bounds.

5. The method according to claim 1, wherein, a real-time dose control algorithm is operated on said suitably programmed computer to provide prospective optimization for an imaging sequence and an imaging technique based on said geometric and topological estimates and uncertainties of said geometric and topological estimates and said planned dose pattern and said accumulative delivery results at an instant of time, wherein said imaging sequence comprises triggers, wherein said imaging technique comprises voltage, tube current and pulse settings.

6. The method according to claim 1, wherein said multimodality input is selected from the group consisting of optical reading, kV/MV imaging, a moveable gantry, radiotherapy beam, and multi-leaf collimator.

7. The method according to claim 1, wherein said method is operated offline and online, wherein said online operation provides in-motion-adaptive image guided radiotherapy used for improving the agreement between planned dose pattern and delivery result, and reduced likelihood of tissue toxicity.

8. The method according to claim 1, wherein uncertainties in said geometric and topological estimates are obtained in real-time by said probabilistic prediction algorithm.

* * * * *